United States Patent
De Paolis et al.

(10) Patent No.: US 7,128,836 B2
(45) Date of Patent: Oct. 31, 2006

(54) DIALYSIS DEVICE

(76) Inventors: Potito De Paolis, 131 Groverton Pl., Los Angeles, CA (US) 90077; Saleh Slehmoghaddam, 159 S. Bowling Green Way, Los Angeles, CA (US) 90049

( * ) Notice: Subject to any disclaimer, the term of this patent is extended or adjusted under 35 U.S.C. 154(b) by 304 days.

(21) Appl. No.: 10/793,792

(22) Filed: Mar. 8, 2004

(65) Prior Publication Data

US 2005/0194304 A1 Sep. 8, 2005

(51) Int. Cl.
B01D 61/28 (2006.01)
A61M 1/14 (2006.01)
B01D 61/26 (2006.01)

(52) U.S. Cl. .............................. 210/321.6; 210/321.72; 422/44; 604/4.01; 604/5.01; 604/5.04

(58) Field of Classification Search ................ 210/209, 210/252, 258, 294, 321.6, 321.64, 321.71, 210/321.72, 645, 646; 435/288.4, 288.5, 435/297.1, 305.2; 422/44; 604/4.01, 5.01, 604/5.04

See application file for complete search history.

(56) References Cited

U.S. PATENT DOCUMENTS

| | | | |
|---|---|---|---|
| 3,701,433 A | 10/1972 | Krukauer et al. | |
| 3,716,372 A * | 2/1973 | De Paolis | 426/46 |
| 3,901,808 A | 8/1975 | Bokros | |
| 3,972,818 A | 8/1976 | Bokros | |
| 4,038,194 A | 7/1977 | Luceyk et al. | |
| 4,147,810 A * | 4/1979 | Kellor | 426/629 |
| 4,213,859 A | 7/1980 | Smakman et al. | |
| 4,289,623 A * | 9/1981 | Lee | 210/247 |
| 4,304,670 A | 12/1981 | Watanabe et al. | |
| 4,352,692 A | 10/1982 | Krinski et al. | |
| 4,490,254 A | 12/1984 | Gordon et al. | |
| 4,650,587 A | 3/1987 | Polak et al. | |
| 5,252,206 A | 10/1993 | Gonzalez | |
| 5,266,215 A | 11/1993 | Engelhard | |
| 5,290,449 A | 3/1994 | Heagle et al. | |
| 5,540,848 A | 7/1996 | Engelhard | |
| 5,979,669 A | 11/1999 | Kitajima et al. | |
| 6,045,699 A | 4/2000 | Yazawa et al. | |
| 6,176,904 B1 | 1/2001 | Gupta | |
| 6,294,380 B1 | 9/2001 | Qiang et al. | |
| 6,328,167 B1 | 12/2001 | Seshimoto et al. | |

(Continued)

FOREIGN PATENT DOCUMENTS

DE 41 18625 C1 10/1992

(Continued)

OTHER PUBLICATIONS www.ghllp.org; The website featured: *First FDA—Cleared Liver Dialysis Treatment* (2 pages) (2003).

(Continued)

*Primary Examiner*—John Kim
(74) *Attorney, Agent, or Firm*—Christopher Wood; Wood & Eisenberg, PLLC (57) ABSTRACT

A dialysis apparatus for treating a patient with liver and/or kidney disease. In one embodiment a liver dialysis apparatus comprises an artificial liver. The artificial liver comprises a blood compartment, a vegetable protein compartment, and a clear dialysis compartment. In another embodiment the liver dialysis apparatus comprises cartridge made up of at least one layer of vegetable protein. In a further embodiment of the invention a dialysate regeneration device is provided which comprises at least one layer of vegetable protein. The vegetable protein is preferably a soy protein. The soy protein may be unmodified soy protein with urease enzyme activity, modified soy protein with or without urease activity, alone or in combination.

13 Claims, 7 Drawing Sheets

U.S. PATENT DOCUMENTS

| | | | |
|---|---|---|---|
| 6,405,875 B1 | 6/2002 | Cutler | |
| 6,451,257 B1 | 9/2002 | Flamer | |
| 6,566,134 B1 * | 5/2003 | Bringe | 435/410 |
| 6,610,027 B1 | 8/2003 | El Hatu | |
| 6,630,068 B1 | 10/2003 | Vinci | |
| 6,635,179 B1 | 10/2003 | Summerton et al. | |
| 6,759,245 B1 * | 7/2004 | Toner et al. | 435/401 |
| 2001/0037079 A1 | 11/2001 | Burbank et al. | |
| 2001/0041892 A1 | 11/2001 | Burbank et al. | |
| 2003/0062300 A1 | 4/2003 | Okano et al. | |
| 2003/0135152 A1 | 7/2003 | Kollar et al. | |
| 2003/0153943 A1 | 8/2003 | Michael et al. | |
| 2003/0196948 A1 | 10/2003 | Bassett et al. | |
| 2004/0081588 A1 * | 4/2004 | Hammerstedt et al. | 422/101 |
| 2004/0099593 A1 * | 5/2004 | De Paolis et al. | 210/266 |

FOREIGN PATENT DOCUMENTS

| | | |
|---|---|---|
| EP | 0 693 296 A1 | 1/1996 |
| EP | 0 693 297 A1 | 1/1996 |
| JP | 7059849 | 3/1995 |

OTHER PUBLICATIONS www.focusonhepe.com; The website featured: *Focus: On Hepatic C International* (3 pages) (2002).

www.organtx.org; The website featured: *Artificial Liver* (13 pages) (2003).

www.physweekly.com; The website featured: *The Artificial Liver* (4 pages) (2000).

http://tellmygene.com; The website featured: *DreamPharm* (6 pages) (2002).

www.ulmedicalgroup.com; The website featured: *Liver Dialysis* (2000).

http://bms.brown.edu; The website featured: *Liver Dialysis Unit from HemoTherapies* (4 pages) (2003).

Gary E. Means and Robert E. Feeney in Chemical Modification of Proteins (publisher: San Francisco, Holden-Day (1971), ISBN: 0-81625-561-X (ASIN: 0816255512), Library of Congress Catalog Card No.: 74-140785); partial copy is attached; pp. 11-20, 32-33, 55-65, 149-174, 220-222.

Nashef et al., Effects of Alkali on Proteins, Disulfides and Their Products, J. Agric. Food Chem., vol. 25, No. 2, (1977), pp. 245-251.

McKinney and Uhing, Carboxymethylated Soybean Protein, J. Amer. Oil Chem. Soc., vol. 36, No. 2, (1959), pp. 49-51.

Chapters five and six of the TAPPI Monograph Series-No. 9, Protein and Synthetic Adhesives for Paper Coating, TAPPI Monograph Series-No. 9, (1952), pp. 84-108.

http://www.northwestern.edu/univ-relations/media_relations/; The website featured: *Clinical trial of "artificial liver" uses albumin dialysis* (2 pages) (2001).

http://www.docguide.com/news/content.nsf/news/8525697700573-E1885256B91004FBD83; This website featured: *Extracorporeal Sorbent Detoxification Saves Lives After Tricyclic Overdosing* (2pages); Apr. 9, 2002.

\* cited by examiner

DIALYSIS DEVICE

CROSS-REFERENCE TO RELATED APPLICATIONS

Not Applicable.

STATEMENT REGARDING FEDERALLY SPONSORED RESEARCH OR DEVELOPMENT

Not Applicable.

FIELD OF THE INVENTION

This invention relates to dialysis. More specifically, the invention relates to a device for treating a patient with liver failure and with minor modification can be used to treat a patient with kidney failure.

BACKGROUND OF THE INVENTION

Treatment options for liver disease are limited. Liver transplantation is the favored treatment for serious liver disease or liver failure. However, the number of suitable liver donors varies and is not always sufficient to meet the demand for liver transplant operations. Thus, there is a need for a way to treat patients with liver failure.

A review of the prior art follows.

The topic of artificial livers is discussed in a world wide web (www) article entitled "Artificial Liver" at URL: http://www.organtx.org/bioart/liver.htm. The article notes that a healthy liver is able to get toxic particles out of the blood by separating them from a sticky carrier protein called albumin. Thus, if the liver fails the toxins stay in the blood and harm nerves, increase pressure in the brain, and damage other important systems. Despite years of research, no machine has been able to remove toxins without harming liver failure patients. One system described is the albumin dialysis system, where albumin is combined with hollow fibers to remove toxins from the blood of a patient with liver problems. Albumin is an animal protein that requires extraction from animals. Animals are known to be source of animal diseases that can harm man. Thus, there is a need for a non-animal sticky protein that can act as an absorbent to remove toxins from the blood of a patient with liver disease.

U.S. Pat. No. 5,866,420 issued Feb. 2, 1999 to Talbot et al., describes continuous cultures of pluripotent parenchymal hepatocytes. In combination with feeder cells and, optionally, adult pig hepatocytes and macrophages, the cells are useful in an artificial liver device which may be utilized as temporary liver support for mitigating the pathological effects of liver failure. The use of cultures of cells of a different genotype, such as pig hepatocytes, raises the prospect of inter-species disease transfer and the emergence of diseases not previously seen in man. A latent virus integrated into the DNA of a pig cell may not show up in a viral screen. Handling and processing cell cultures is complicated and would add to the cost of the treating a liver failure patient. In addition, the '420 patent does not teach or suggest, for example, using soybean protein to treat blood from a patient with liver disease.

U.S. Pat. No. 6,653,105 issued Nov. 25, 2003 to Triglia et al., describes a serum-free C3A clonal cell line of possible use in a bio-artificial liver device. The '105 cell line is a liver cell line similar to the cell line described in U.S. Pat. No. 5,290,684. The cell line exhibits liver-specific activity and may therefore be of use in a bio-artificial liver device to treat a patient having or suspected of having a liver condition, liver related disorder or compromised liver function resulting either from disease or trauma (e.g. Fulminate hepatic failure (FHF), awaiting liver transplant or following liver rejection and awaiting liver retransplant). Maintaining the viability of the serum-free C3A clonal cell line is complicated and requires a high level of specialist skill not generally found in a liver failure unit in a general hospital. Therefore, there is a need for a device to treat patients with a liver condition, or suspected liver condition, that does not rely on maintaining a viable line of liver cells in an artificial environment.

U.S. Pub. No. 20030153943 published Aug. 14, 2003 to Michael et al., describes a medical device, such as a vascular filter, and a method of making the same. The vascular filter is composed of: a reinforced membrane unit composed of: a thin filter membrane, and fibers of reinforcement material embedded in the membrane to strengthen the filter and securely attach the fibers to the membrane. The method of fabricating comprises the steps of: providing a mold that can be melted, dissolved, or deformed without damaging membrane material; covering the mold with an intermediate material that is easily separated from the membrane material; covering the intermediate material with the membrane material; placing the fibers in contact with the membrane material that covers the intermediate material; covering the fibers with additional membrane material to form the membrane with embedded fibers; removing the mold by melting, dissolving, or deforming the mold; and removing the intermediate material from the membrane. The '943 device and method does not teach or suggest, for example, using soybean protein in the treatment of a patient with actual or suspected liver disease.

U.S. Pat. No. 6,294,380 issued Sep. 25, 2001 to Qiang et al., describes a blood perfusion device used for bioartificial liver support. Human hepatocyte lines established from normal regenerating liver tissue and modulated in toxin-challenging conditions are provided. These functional hepatocytes exhibit extraordinarily enhanced detoxification functions, which are characterized by the elevated glutathione content and glutathione S-transferase activity. A bioreactor is constructed with the functional hepatocytes for bioartificial liver support system, which includes perfusion inlets and perfusion outlets, a containment vessel, a centrifugal pump and macroporous microcarriers where the functional hepatocytes are grown. Relying on human hepatocyte lines to treat a liver patient's blood is complicated and requires a high level of specialist skill.

U.S. Pat. No. 3,972,818 issued Aug. 3, 1976 to Bokros, describes a device for treating human blood prior to its return to a living human body. The blood filter employs a bed of fibers between about 1 and 100 microns in diameter, the outer surface of which is formed of impermeable carbon. Suitable fibrous substrates may be coated with vapor-deposited pyrolytic carbon, and the fibers may be supported between similarly coated upper and lower screens. The '818 device does not teach or suggest the subject matter of the present invention.

None of the above inventions and patents, taken either singly or in combination, is seen to describe the present invention as claimed.

SUMMARY OF THE INVENTION

The invention is directed to a dialysis apparatus for treating a patient with liver and/or kidney disease. In one embodiment a liver dialysis apparatus comprises an artificial liver. The artificial liver comprises a blood compartment, a vegetable protein compartment, and a clear dialysis compartment. In another embodiment the liver dialysis apparatus comprises cartridge made up of at least one layer of vegetable protein. In a further embodiment of the invention a dialysate regeneration device is provided which comprises at least one layer of vegetable protein. The vegetable protein is preferably a soy protein. The soy protein may be unmodified soy protein with urease enzyme activity, modified soy protein with or without urease activity, alone or in combination.

BRIEF DESCRIPTION OF THE DRAWINGS

Similar reference characters denote corresponding features consistently throughout the attached drawings.

DETAILED DESCRIPTION OF THE PREFERRED EMBODIMENTS

Specific structural and functional details disclosed hereby are not to be interpreted as limiting, but merely as providing a proper basis for the claims and as a representative basis for teaching one of ordinary skill in the art how to practice the invention.

The present invention is particularly directed to a device that comprises at least one layer of vegetable protein for removing toxic agents from the blood of a patient with a dysfunctional liver and/or dysfunctional kidney. The vegetable protein may be substantially unmodified or chemically modified with or without urease enzyme activity. The vegetable protein is preferably a legume protein derived from the seeds of leguminous plants such as soybean, cottonseed, peanut, tung nut, castor bean, and linseed, alone or in combination.

In one embodiment of the invention, the protein is substantially unmodified soy protein containing active urease enzyme. In another embodiment of the invention, the protein is chemically modified soy protein substantially free of urease enzyme activity. In a still further embodiment of the invention, the soy protein is chemically modified soy protein with added urease enzyme activity.

Soybean is known to be a very healthy legume that contains a high amount of healthy protein that is not normally toxic to man and is necessarily substantially free of animal or liver related disease agents such as the causative agent of hepatitis. Soy protein offers a far safer alternative to animal or human albumin that could harbor undesirable disease agents.

Vegetable protein such as soy protein is made up of amino acids linked together to form a three dimensional structure. At least some of the vegetable protein amino acids are hydrophilic such as the serine and threonine amino acids. At least some of the vegetable protein amino acids are hydrophobic such as phenylalanine, leucine and isoleucine. Other amino acids may be charged such as aspartate and lysine, which at physiological pH are respectively negatively and positively charged. (The ionic states of amino acid side chains as a function of pH are found, for example, on page 14 in Chemical Modification Of Proteins (Authors: Gary E. Means and Robert E. Feeney, publisher: San Francisco, Holden-Day [1971], ISBN: 0-81625-561-X, Library of Congress Catalog Card Number: 74-140785).

The vegetable amino acids are able to bind to molecules by means of a variety of non-covalent intermolecular binding interactions including hydrogen bonding and other electrostatic interactions, hydrophobic bonding, and non-polar Van der Waal interactions. For example, an amino acid with a side-chain that exhibits a net negative charge has a strong affinity for a liver toxic molecule with a positive charge. Conversely, a vegetable amino acid with a side chain having a positive charge at a specific pH (e.g., lysine) would bind to a liver toxic molecule with a negative charge. Amino acids with non-polar aliphatic side chains such as leucine, isoleucine and valine would tend to non-covalently bind to hydrophobic molecules or hydrophobic parts of molecules. Thus, a vegetable protein molecule comprises of numerous residues, i.e. amino acid side-chains, which are available for binding to toxic molecules.

To render more of the amino-acid side chains of the soy protein molecules available to bind to toxic molecules, the soy protein can be chemically modified in vitro to modify the binding properties of specific side-chains; disulfide bond breaking agents, such as the reducing agent ammoniumthioglycolate (ATG), may be used to break —S—S— bonds to help denature the soy protein molecules to expose internal amino acids for binding to toxic molecules. Other methods of altering the shape of soy protein are well known and include alkaline hydrolysis, which also breaks the protein backbone at random points to produce variable length soy polypeptides.

Since it is important that the dialysate is not contaminated with low molecular weight soy polypeptides (for example, under 10,000 Daltons) the amount of hydrolysis should be limited. SDS polyacrylamide gel electrophoresis (SDS-PAGE) along with appropriate molecular weight markers can be used to check the size distribution of the hydrolyzed Soy protein. Unsuitable polypeptide lengths can be selectively discarded using established techniques such as dialysis based on, for example, permeable membranes with molecular weight cut-offs of around 10,000 Daltons to remove the unwanted lower molecular Soy molecules.

It will be understood that the molecular weight of the unwanted polypeptides can vary according to the molecular weight cut-offs of the permeable membranes used in the invention. For example, if the membranes have a 5,000 Dalton cut-off, the unsuitable molecular weight range would be less than about 5,000 Daltons. Thus, the invention is not restricted to making use of peptides of greater than 10,000 Daltons, but may make use of lower molecular weight peptides based on the cut-off of the membranes used in the dialysis apparatus according to the invention.

In addition to breaking —S—S— bonds, the vegetable protein may be further chemically modified using a variety of known techniques and reagents. The terms "chemically modified" or "chemical modification" are used herein to encompass any treatment, such as hydrolysis, carboxylation, oxidation, precipitation or additional separation, which occurs after the vegetable protein material is extracted. The field of chemical modification of proteins is well known in the art and is reviewed, for example, in: (1) Gary E. Means and Robert E. Feeney in Chemical Modification Of Proteins (publisher: San Francisco, Holden-Day (1971), ISBN: 0-81625-561-X, Library of Congress Catalog Card Number: 74-140785); (2) Nashef et al., Effects of Alkali on Proteins, Disulfides and Their Products, J. Agric. Food Chem., Vol. 25, No. 2, (1977), pp 245–251; and (3) McKinney and Uhing, Carboxymethylated Soybean Protein, J. Amer. Oil Chem. Soc., Vol. 36, No. 2, (1959), pp 49–51. The Means and Feeney, Nashef, and McKinney references are hereby incorporated by reference in their entirety.

Isolated unmodified soy protein may be prepared by selecting dehulled soybeans that are cracked and flaked for extraction of oil by means of solvent. The oil extraction process and subsequent removal of solvent from the flakes are carried out without undesirable alteration of the protein present in the flakes. To isolate the unmodified protein, 1 part of substantially oil-free flakes is slurried with 10 to 20 parts of water and a small amount of alkali is added to increase the solubility of the soy protein. The solution containing the extracted protein is then usually separated from the flake residue by means of shaker screens. The screened solution is subjected to filtration or centrifugation to remove flake fines, and the protein is precipitated from the solution, in the isoelectric range of the protein (usually in the pH range of about 4.0 to 4.5), by means of acid. The protein curds obtained are dewatered and dried to provide unmodified soy protein. Specifically, after the isoelectric precipitation step the unmodified soy protein curd can be dried to produce a granulated dried protein of greater than 95% purity. Typically, this soy isolate, which has not otherwise been heated or chemically modified in some fashion, will contain a significant amount of urease enzyme activity, which is an inherent component of uncooked or unmodified soy protein. The natural urease activity enables the soy protein to convert urea into ammonia, and may be used in the invention as described below. For further information see, for example, U.S. Pat. No. 4,352,692 (issued Oct. 5, 1982 to Krinski et al); the '692 patent is hereby incorporated by reference in its entirety. In addition, the manufacture and chemistry of isolated soy protein is discussed in chapters five and six of the *TAPPI Monograph Series-No.* 9 (PROTEIN and SYNTHETIC ADHESIVES for Paper Coating, *TAPPI Monograph Series-No.* 9, (1952), pp 84–108); chapters five and six are herein incorporated by reference in their entirety.

Urease enzyme activity can also be maintained in soy protein that has been modified by adding urease to the modified protein. For example, the soy protein may be oxidized and provided with urease activity by carrying out the following steps: (1) forming a slurry of a urease containing unmodified soy protein with a proteinaceous solids content of 10 to 30% by weight; (2) adding to the slurry a sufficient amount of urea to react with the urease therein to produce ammonia sufficient to increase the pH of the slurry to a value above about pH 8.0; (3) adding an oxidizing agent to the slurry in an amount and for a time sufficient to improve the rheological properties by lowering the viscosity of the protein material; and (4) adding urease enzyme back into the oxidized (i.e., modified) slurry to provide a modified soy protein slurry with urease activity; and (5) gently drying the modified urease containing soy protein slurry for later incorporation into a liver or kidney dialysis device of the present invention. If the modified soy protein is intended to treat a patient with abnormal liver function and normal kidney function, the modified soy protein need not contain urease activity; therefore, step (4) may be skipped, i.e. urease enzyme need not be added to the modified soy protein. In addition, the types of soy protein may be mixed, e.g. modified with unmodified soy protein. Thus, it should be clear that the soy protein component may vary in form: unmodified urease containing soy protein, modified soy protein lacking urease activity, modified soy protein with urease activity, alone or in combination. It will be understood that the handling and processing of the soy protein should be undertaken to meet the appropriate legal standards, including but not limited to: use of a clean facility, and practicing where possible aseptic technique to avoid contaminating the soy protein with undesirable matter.

Referring now to the figures.

Figure 1:
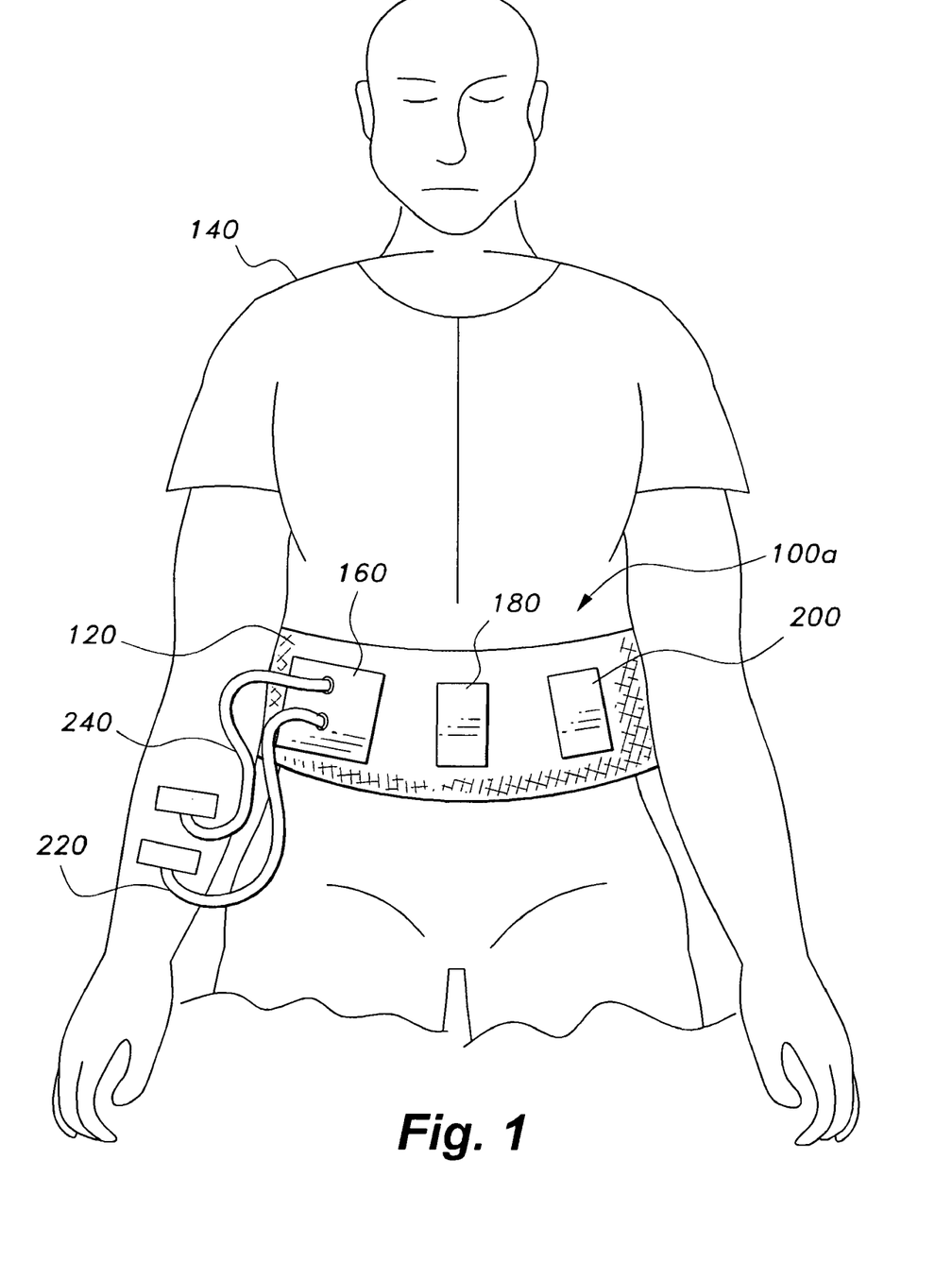
FIG. 1 is an environmental perspective view of a mobile liver dialysis device integrated into the design of a belt according to the present invention.

FIG. 1 shows one embodiment of the present invention. Specifically, a liver dialysis device 100 (represented by the alpha-numeric label "100*a*") is shown integrated into a belt 120 that can be worn by a patient 140 with liver disease or suspected liver disease. Visible in the belt 120 is an artificial liver 160, a regeneration device 180 that purifies the dialysis liquid (dialysate), and a power supply 200. Tubes 220 and 240 provide appropriate arterial and venous access between the artificial liver 160 and the patient 140. If necessary, the extracorporeal transport of the patient's blood through tubes 220 and 240 may be assisted by a blood pump 380 (see FIG. 3A); the blood flow rate should be at least about 250 milliliters per minute (ml/min), and preferably in the range between about 250 ml/min and about 500 ml/min.

Figure 2:
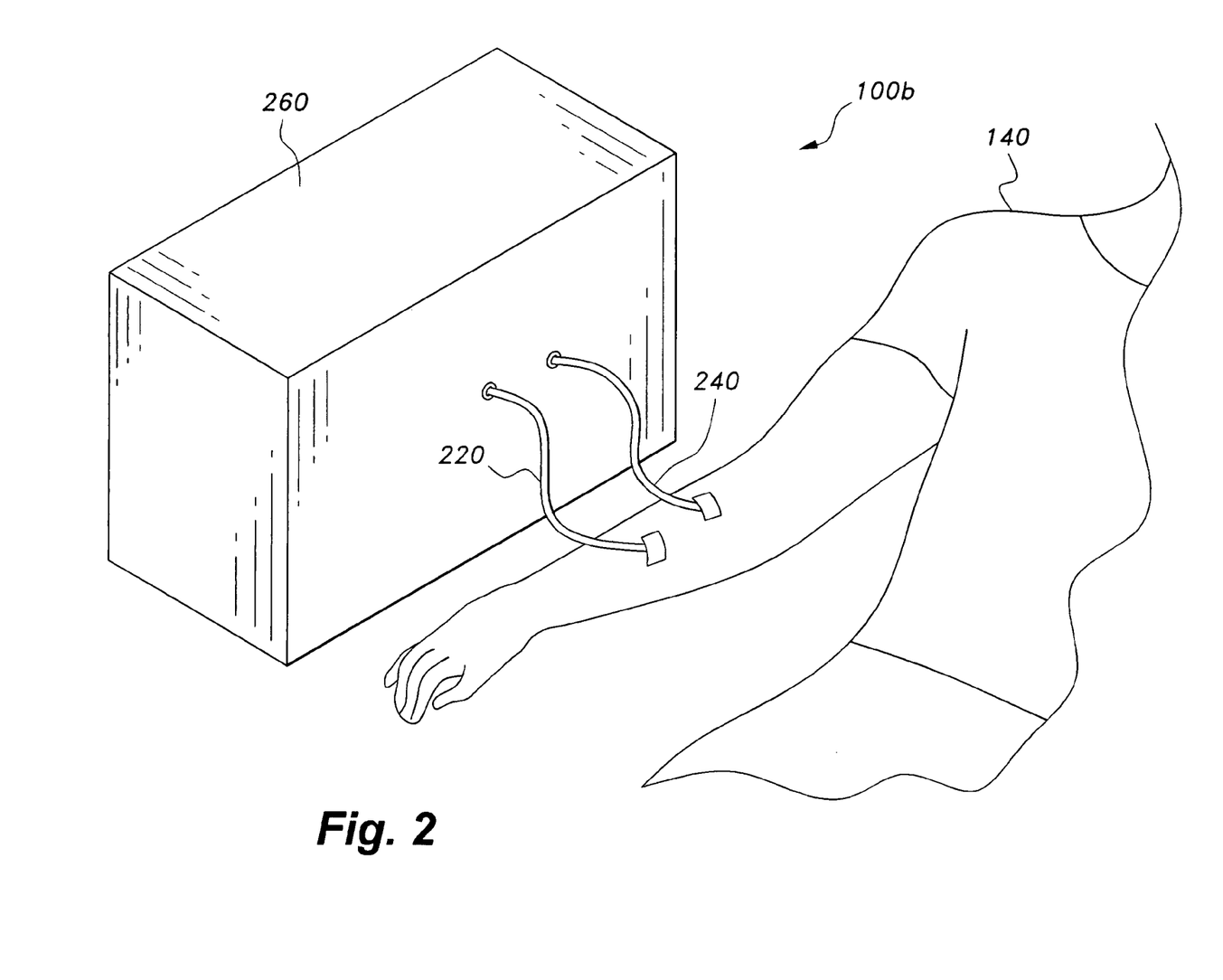
FIG. 2 is an environmental perspective view of a compact sized liver dialysis device according to the present invention.

FIG. 2 shows another embodiment of the present invention. Specifically, a liver dialysis device 100 (represented by the alpha-numeric label "100*b*") is shown integrated into a housing 260. The device 100*b* is shown positioned next to a liver patient 140.

Figure 3A:
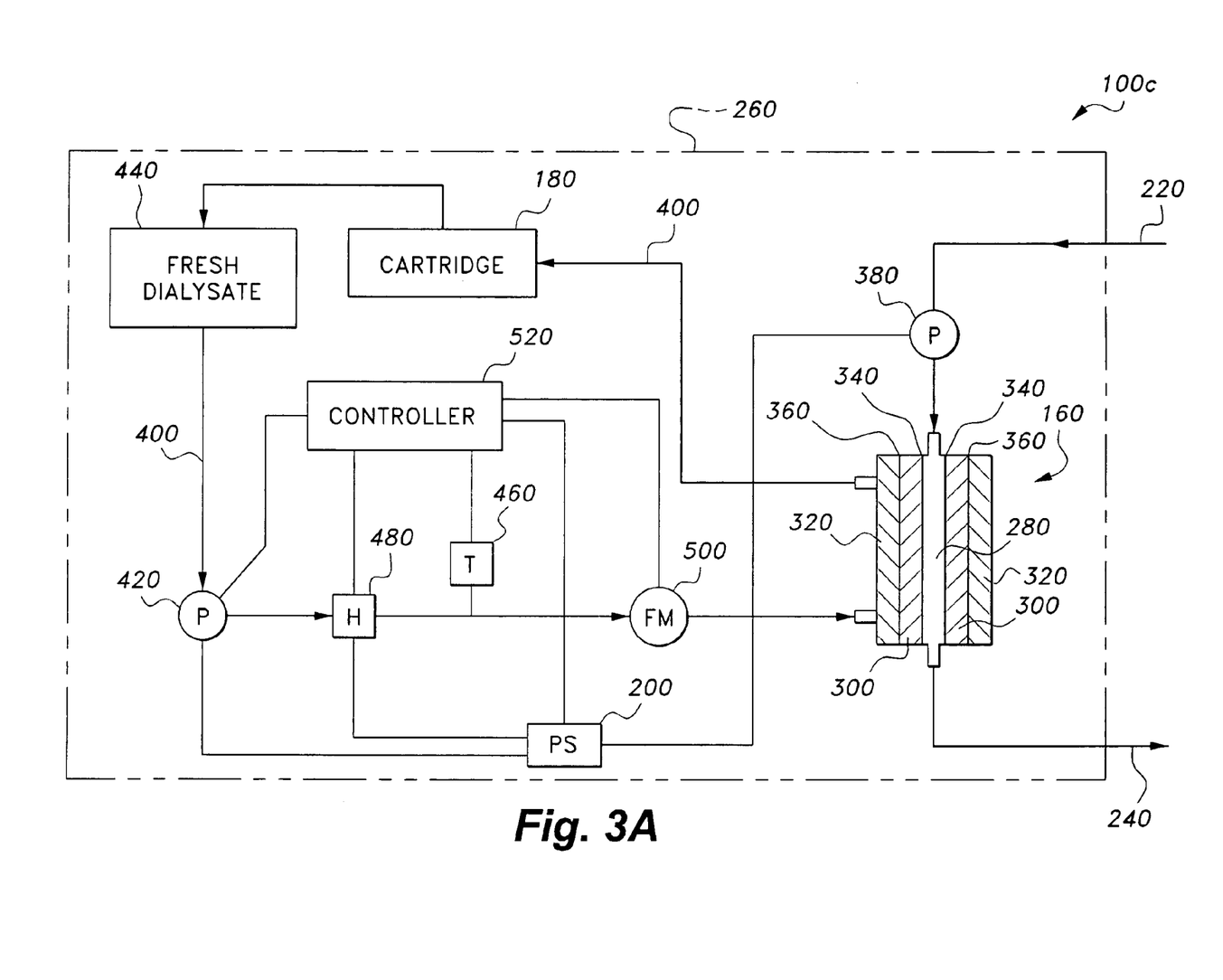
FIG. 3A is a schematic representation of a liver dialysis device according to the present invention.
Figure 3B:
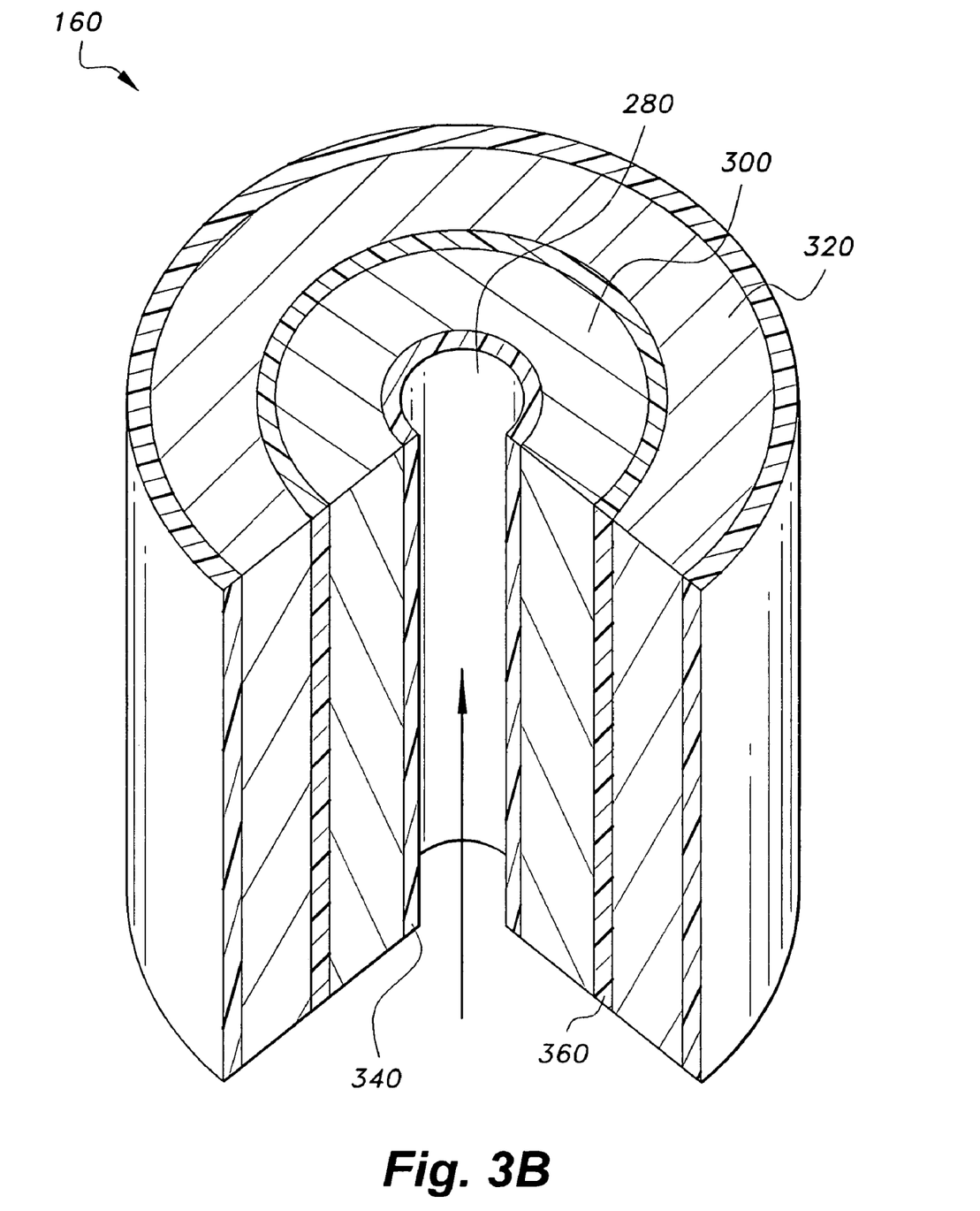
FIG. 3B shows a partially cut-away view of an artificial liver according to one aspect of the present invention.

FIG. 3A is a schematic representation of a liver dialyzer device 100 (represented by the alpha-numeric label "100*c*"). An artificial liver 160 is shown comprising at least one blood compartment 280, a soy protein compartment 300, and a clear dialysis compartment 320. A first selectively permeable membrane 340 separates compartments 280 and 300. A second selectively permeable membrane 360 separates compartments 300 and 320. The membranes 340 and 360 may be in any suitable form, for instance in that of flat or tubular film (see FIG. 3B), or it may comprise a large number of hollow fibers. The blood compartment 280 is connected to the circulatory system of a patient 140 by means of tubes 220 and 240. If necessary, the extracorporeal transport of the blood may be assisted by a blood pump 380. The blood pump 380 may be integrated into the design of, for example, the artificial liver 160.

Dialysis liquid flows through compartment 320 and circulates through a dialysis circuit 400 by means of a dialysate pump 420. Dialysate enters compartment 300 from compartment 320 thereby allowing an interchange across membrane 340. The molecular weight of the protein molecules inside compartment 300 are such that they are unable to penetrate membranes 340 or 360, but smaller molecules that don't bind to the protein are able to transfer across membrane 340 and into circuit 400 for selective removal by the dialysate regeneration device 180.

Figure 3C:
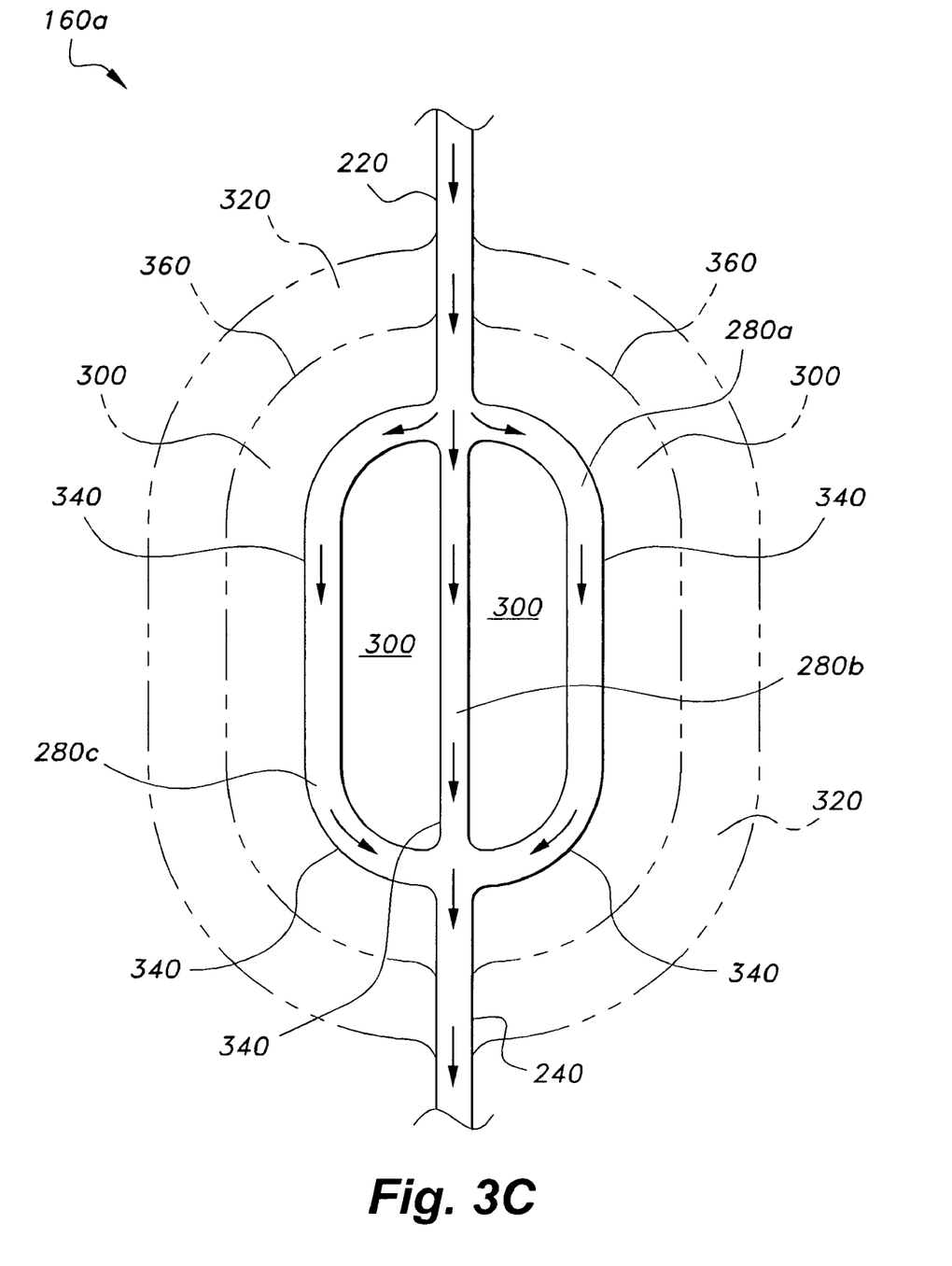
FIG. 3C is a schematic representation of an artificial liver that comprises more than one blood compartment.

It should be understood that the exact arrangement and layout of the artificial liver 160 might vary. For example, FIG. 3C shows an artificial liver 160 (shown as 160*a*), wherein the tube 220 directs patient blood to more than one blood compartment 280 (shown as 280*a*, 280*b*, and 280*c*). Since volume increases by the cube and surface area by the square the ratio of surface area to volume ratio is more favorable as volume decreases. Thus, the rate of exchange across membrane 340 improves with lower cross section area of the at least one blood compartment 280. However, the cross section area of the at least one blood compartment 280 should be sufficient not to obstruct the flow of blood through blood compartment 280.

It will be understood that the order and arrangement of the various functional members in the dialysis circuit 400 may vary. For example, the dialysate pump 420 may be integrated into the design of the regeneration device 180. The location of the flow meter 500 may also vary without detracting from the spirit of the present invention.

It should be understood that the term "clear" as used in "clear dialysis compartment 320" is intended to mean "substantially clear of soy protein"; the membrane 360 serves to allow the interchange of dialysate between the compartments 300 and 320 while preventing transfer of soy protein molecules from soy protein compartment 300 into clear dialysate compartment 320; incidentally, membrane 340 prevents transfer of soy protein molecules from soy protein compartment 300 into blood compartment 280. Toxic molecules from the blood compartment 280 transfer into the soy protein compartment 300 for absorption by the soy protein held therein, toxic molecules not absorbed are free to transfer across membrane 360 into the clear dialysate compartment 320 which forms part of the dialysis circuit 400.

The membrane 340 is rated to be impermeable to blood cells, including white and red blood cells, but is permeable to electrolytes and molecules up to about 10,000 Daltons. The membrane 360 is preferably permeable to electrolytes and molecules up to about 10,000 Daltons; however, the molecular weight cut-offs of the membranes 340 and 360 can be dissimilar. Also, the membranes 340 and 360 may be dissimilar and may separately take the form of a flat or tubular film, or hollow fibers. Waste products not absorbed by the soy protein in compartment 300 are transferred across the membrane 360 into the clear dialysate compartment 320. The soy protein may be unmodified soy protein with urease activity, modified protein with urease activity, and modified protein absent urease activity, alone or in combination. It is preferred that if the patient 140 is not suffering from kidney failure (i.e. liver failure absent kidney failure) the soy protein is modified protein absent urease activity.

Still referring to FIG. 3A, dialysis circuit 400 comprises a regeneration device 180 adapted to purify the dialysate (dialysis liquid) from the waste products it has taken up from compartment 300. More specifically, the device 180 converts used dialysate back into "fresh" or reconstituted dialysate. The regeneration device 180 may consist of several layers connected in series or in parallel, which each serve to eliminate one or more waste products. The cartridge may be of conventional design such as the REDY™ purification cartridge as used in the REDY™ dialysis system. The REDY™ purification cartridge comprises five layers through which used dialysate passes: (i) a purification layer comprising of activated charcoal; (ii) an enzyme layer comprising of urease; (iii) a cation exchange layer comprising of zirconium oxide; (iv) and anion exchange layer comprising of hydrated zirconium oxide; and (v) an absorbent layer comprising again of activated charcoal. Organon Teknika Corporation of Oklahoma City, Okla., USA, supplies the REDY™ dialysis system. Alternatively, the regeneration device 180 may comprise a layer of vegetable protein such as soy protein (unmodified, modified with or without urease enzyme activity, alone or in combination); the layer of vegetable protein may replace or act as a partial substitute for the activated charcoal layer normally found in conventional dialysate regeneration cartridges such as that used in the REDY™ dialysis system. The layers in device 180 may be in series or in parallel.

When urease enzyme activity is present in the vegetable protein in compartment 300 the regeneration device 180 need not have a layer comprising of urease enzyme. Specifically, when the vegetable protein is unmodified vegetable protein with urease activity and/or modified protein with added urease activity there is no requirement for a separate layer of urease activity in device 180. For example, the regeneration device 180 may comprise of four layers: (i) a purification layer comprising of activated charcoal; (ii) a cation exchange layer comprising of zirconium oxide; (iii) and anion exchange layer comprising of hydrated zirconium oxide; and (iv) an absorbent layer comprising again of activated charcoal. Preferably the charcoal layers are left out or diminished in device 180; for example, the regeneration device 180 may be made of just three layers: (i) a cation exchange layer comprising of zirconium oxide; (ii) an anion exchange layer comprising of hydrated zirconium oxide; and (iii) a layer comprising activated charcoal.

Where ammonia remains a problem due to urease activity an ammonia scavenger may be incorporated into device 180, e.g. as a separate layer comprising of ammonia scavenger or mixed with another layer in device 180. Any suitable ammonia scavenger may be used such as a particulate magnesium phosphate product as described in U.S. Pat. No. 4,650,587 (issued Mar. 17, 1987 to Polak et al) with the general formula $(Mg)_x(H)_y(PO_4)_z$, wherein when "z" has an assigned value of 1, "x" has a value greater than 1, and about 1.1 to about 1.3, and "y" has a value less than 1 and about 0.4 to about 0.8; the '587 reference is hereby incorporated by reference in its entirety.

Still referring to FIG. 3A, in the dialysis circuit 400 there are: a dialysate pump 420, an optional vessel 440 to hold reconstituted dialysate, dialysate temperature probe 460, a dialysate heater 480, and a flow meter 500. It should be understood that the order of devices in the circuit 400 may vary; additionally, the devices may be integrated into single functional members, e.g., the temperature probe 460 and heater 480 might be integrated and operated under the control of a dedicated temperature controller. The terms "reconstituted dialysate" and "fresh dialysate" are regarded as equivalent terms.

The devices 420, 460, 480, 500 are monitored and/or operated by a controller 520 adapted to perform logic operations based on a control algorithm. For example, the controller 520 monitors and controls the function of the pump 420 (in response to data received from, for example, the flow meter 500), and heater 480 is switched on or off (in response to data received from the temperature probe 460). A power supply 200 is connected to all parts that require power such as, for example, the controller 520 and dialysate pump 420.

Figure 4A:
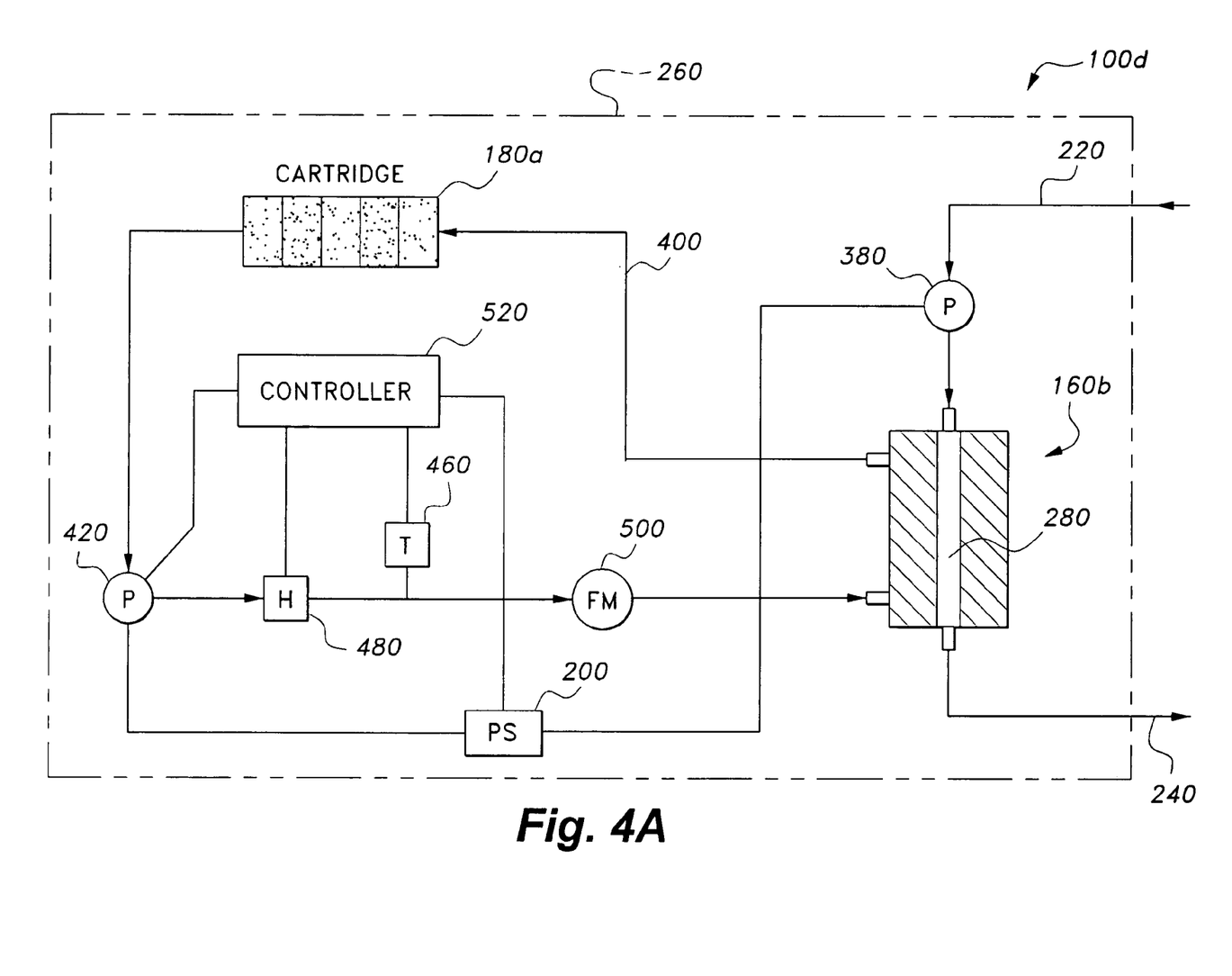
FIG. 4A is a schematic representation of a dialysis system that employs an unconventional dialysate regeneration cartridge according to the present invention.

FIG. 4A is a schematic representation of a further embodiment of the present invention 100d employing a novel dialysate regeneration cartridge 180a; the cartridge 180a comprises at least one layer of vegetable protein such as soy protein. The dialysate regeneration cartridge 180a is used in conjunction with a dialyzer of conventional design (represented by the alpha-numeral "160b"). The conventional dialyzer 160b operates much in the same way as an artificial kidney as described in column 6, lines 44–56 in U.S. Pat. No. 4,213,859 (issued Jul. 22, 1980 to Smakman et al); the '859 patent is hereby incorporated by reference in its entirety.

Figure 4B:
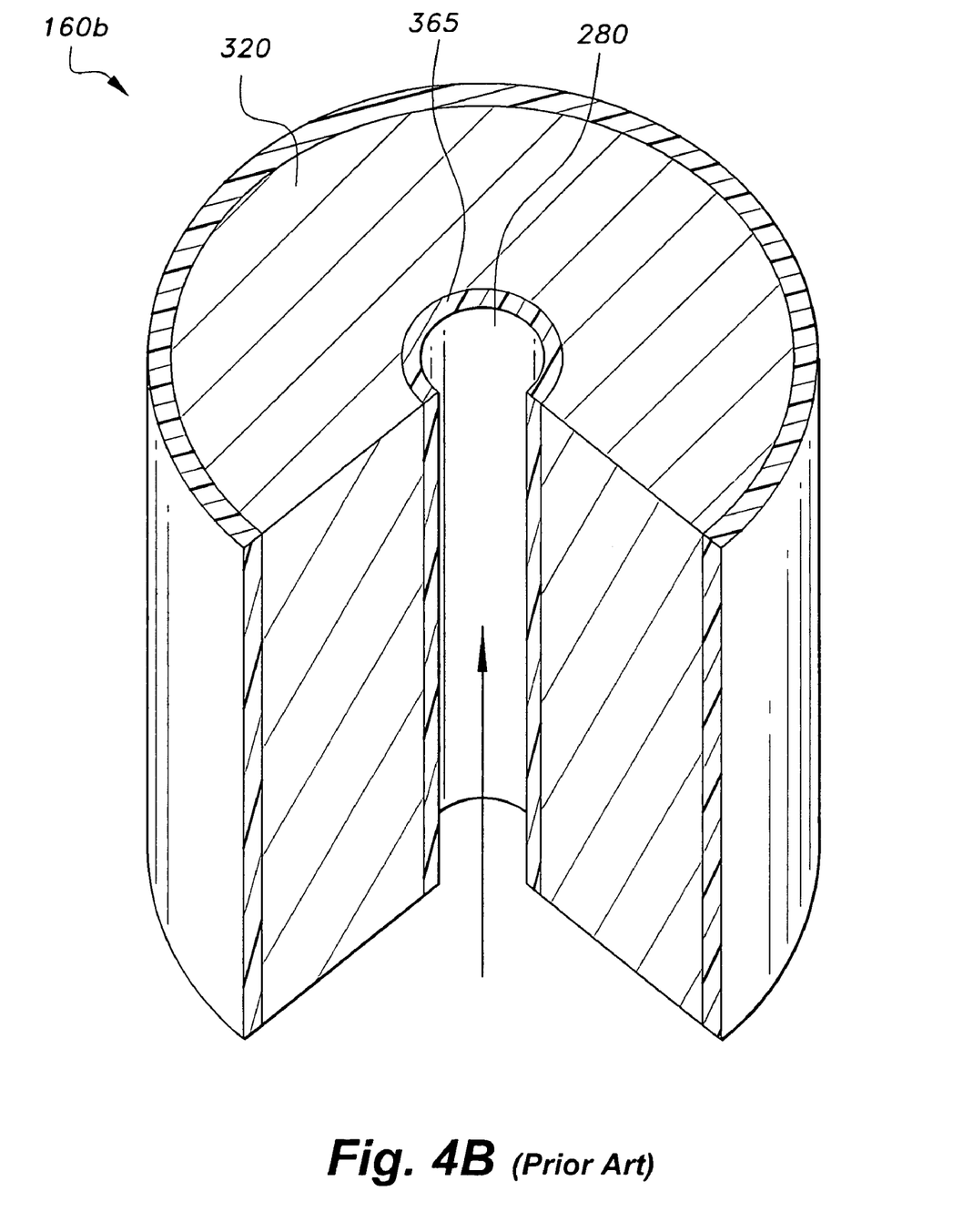
FIG. 4B shows a partially cut away view of a dialyzer of conventional design.

FIG. 4B shows a partially cut away view of dialyzer 160b. Dialyzer 160b has a blood compartment 280 and a clearance or dialysis compartment 320 separated by a selectively permeable membrane 365. The membrane 365 may be in any desirable form, for instance in that of flat or tubular film, or it may be a large number of hollow fibers. Dialysis liquid flows through compartment 300 and circulates through the dialysis circuit 400 as shown in FIG. 4A.

The dialysate regeneration device 180a comprises at least one layer of vegetable protein. The vegetable protein may be unmodified or modified soy protein with or without urease enzyme activity. The layer of vegetable protein may replace or complement a charcoal layer as found in the REDY™ purification cartridge. For example, the dialysate regeneration cartridge 180a may comprise of the following layers: (i) a layer of vegetable protein; (ii) a cation exchange layer comprising of zirconium oxide; (iii) and anion exchange layer comprising of hydrated zirconium oxide; and (iv) a layer comprising of activated charcoal.

The composition of the layer of vegetable protein in cartridge 180a may vary. Cartridge 180a may comprise a layer of modified or unmodified soy protein with or without urease enzyme activity. The layer of vegetable protein may be made of a combination of modified and unmodified soy protein with or without urease enzyme activity. The order of layers with respect to dialysate flow may vary, though it is preferable to have a purification layer downstream of the cation and anion exchange layers, e.g. a layer of activated charcoal downstream of the ion exchange layers. Dialysate regeneration device 180a enables a conventional dialyzer 160b to be used to treat a patient 140 with liver and/or kidney disease.

It is to be understood that the present invention is not limited to the embodiments described above, but encompasses any and all embodiments within the scope of the following claims.

We claim:

1. An artificial liver for use in a liver dialysis apparatus, comprising:
   a blood compartment, wherein during use the blood compartment is connected to the blood circulatory system of a patient;
   a vegetable protein compartment adjacent to the blood compartment, wherein the vegetable protein compartment contains vegetable protein; and
   a clear dialysis compartment adjacent to the vegetable protein compartment, wherein during use the clear dialysis compartment is attached to a dialysis circuit
   wherein a first selectively permeable membrane separates the blood and vegetable protein compartments and a second selectively permeable membrane separates the vegetable protein and the clear dialysis compartments,
   wherein during use of the artificial liver, toxic molecules found in the blood compartment transfer to the vegetable compartment for absorption,
   wherein the first selectively permeable membrane is impermeable to blood cells, including white and red blood cells, and is impermeable to vegetable proteins contained in the vegetable protein compartment, and
   wherein the second selectively permeable membrane is impermeable to vegetable proteins contained in the vegetable protein compartment.

2. The artificial liver for use in a liver dialysis apparatus according to claim 1, wherein the vegetable protein is unmodified soy protein with urease activity.

3. The artificial liver for use in a liver dialysis apparatus according to claim 1, wherein the vegetable protein is essentially unmodified soy protein with urease activity.

4. The artificial liver for use in a liver dialysis apparatus according to claim 1, wherein the vegetable protein is modified soy protein lacking urease enzyme activity.

5. The artificial liver for use in a liver dialysis apparatus according to claim 1, wherein the vegetable protein is modified soy protein in combination with active urease enzyme capable of converting urea into ammonia.

6. The artificial liver for use in a liver dialysis apparatus according to claim 1, wherein the first selectively permeable membrane is permeable to electrolytes and molecules up to about 5,000 Daltons.

7. The artificial liver for use in a liver dialysis apparatus according to claim 1, wherein the first selectively permeable membrane is permeable to electrolytes and molecules up to about 10,000 Daltons.

8. A liver dialysis apparatus for the purification of blood or bodily fluid from a patient with a liver disorder or suspected liver disorder, the apparatus comprising:
   an artificial liver comprising a blood compartment, a vegetable protein compartment, and a clear dialysis compartment, wherein a first selectively permeable membrane separates the blood and vegetable protein compartments and a second selectively permeable membrane separates the vegetable protein and the clear dialysis compartment, and the vegetable protein compartment contains vegetable protein; and
   a dialysate circuit, comprising a dialysate purification cartridge and a dialysate pump,
   wherein the dialysate circuit is connected to the clear dialysis compartment,
   wherein during use of the artificial liver, toxic molecules found in the blood compartment transfer to the vegetable compartment for absorption,
   wherein the first selectively permeable membrane is impermeable to blood cells, including white and red blood cells, and is impermeable to vegetable proteins contained in the vegetable protein compartment, and
   wherein the second selectively permeable membrane is impermeable to vegetable proteins contained in the vegetable protein compartment.

9. The liver dialysis apparatus according to claim 8, wherein the vegetable protein is unmodified soy protein with urease activity.

10. The liver dialysis apparatus according to claim 8, wherein the vegetable protein is essentially unmodified soy protein with urease activity, and wherein the dialysate regeneration device further comprises an ammonia scavenger compound.

11. The liver dialysis apparatus according to claim 8, wherein the vegetable protein is modified soy protein lacking urease enzyme activity.

12. The liver dialysis apparatus according to claim 8, wherein the vegetable protein is modified soy protein in combination with active urease enzyme capable of converting urea into ammonia.

13. An artificial liver for use in a liver dialysis apparatus, comprising:
   a blood compartment, wherein during use the blood compartment is connected to the blood circulatory system of a patient;

a vegetable protein compartment adjacent to the blood compartment, wherein the vegetable protein compartment contains vegetable protein; and a clear dialysis compartment adjacent to the vegetable protein compartment, wherein during use the clear dialysis compartment is attached to a dialysis circuit, wherein a first selectively permeable membrane separates the blood and vegetable protein compartments and a second selectively permeable membrane separates the vegetable protein and the clear dialysis compartments, wherein during use of the artificial liver toxic molecules found in the blood compartment transfer to the vegetable compartment for absorption, wherein the first selectively permeable membrane has a molecular weight cut-off of about 10,000 Daltons, and wherein the second selectively permeable membrane has a molecular weight cut-off of about 10,000 Daltons.

* * * * *